United States Patent [19]

Giudicelli et al.

[11] 4,011,330
[45] Mar. 8, 1977

[54] VINCAMINIC ACID AMIDES

[75] Inventors: Don Pierre René Lucien Giudicelli, Fontenay-sous-Bois; Henry Najer, Paris; Patrick Andre Louis Lardenois, Gentilly; Jean Pierre Gaston Lefevre, Paris; Bogdan Iliesco-Branceni, Paris; Icilio Angelo Girolamo Cavero, Paris, all of France

[73] Assignee: Synthelabo, Paris, France
[22] Filed: June 23, 1975
[21] Appl. No.: 589,088
[30] Foreign Application Priority Data
  Sept. 24, 1974  France .................. 74.32095
  May 26, 1975   France .................. 75.16290
[52] U.S. Cl. .................. 424/266; 260/293.53; 424/267
[51] Int. Cl.² .................. C07D 471/04
[58] Field of Search .......... 260/293.53; 424/267, 424/266

[56]        References Cited
        UNITED STATES PATENTS
3,891,640  6/1975  Plat et al. .............. 260/247.5 FP Primary Examiner—G. Thomas Todd
Attorney, Agent, or Firm—Armstrong, Nikaido & Wegner

[57]        ABSTRACT

The invention provides compounds of formula

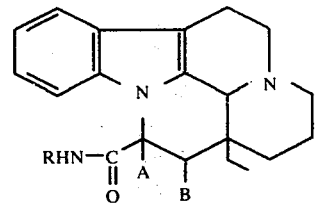

wherein A and B are hydrogen and R is hydrogen or cycloalkyl, or A and B together form an additional bond and R is cycloalkyl or cycloalkyl-alkyl. Useful in treating pathological disturbancies involving an anoxia factor.

15 Claims, No Drawings

VINCAMINIC ACID AMIDES

The present invention relates to compounds which are amides of apovincaminic acid and desoxyvincaminic acid, to a process for their preparation and to their application in therapy.

The compounds of the invention have useful therapeutic properties which make it possible to use them for the treatment of pathological disturbances involving an anoxia factor, particularly at the level of the central nervous system.

Certain amides of these two acids have already been described in the literature, for example in French Pat. Nos. 2,023,918, 2,176,516 and 2,211,225.

The compounds of the invention have the general formula (I)

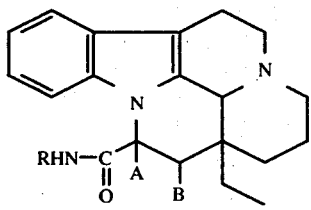

in which A and B are hydrogen atoms and R is a hydrogen atom or a

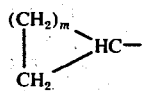

group, or A and B together represent an additional bond and R is a

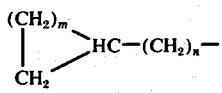

group, $m$ being 1, 2, 3 or 4 and $n$ being 0, 1, 2 or 3, or a pharmaceutically acceptable acid addition salt with an inorganic or organic acid.

According to the invention, the amides can be prepared by reacting a halide of apovincaminic acid or desoxyvincaminic acid with an amine of formula $RNH_2$.

This reaction can be carried out either in a neutral medium or in a basic medium, in a non-polar solvent, and if appropriate in the presence of an acceptor for hydrogen halide acids; an example of such an acceptor is a tertiary organic base, for example pyridine.

The acid halide can be obtained in conventional manner by reacting the acid or an alkali metal salt thereof, with a thionyl halide or oxalyl halide for example the chloride.

This reaction is preferably carried out in a non-polar solvent, such as 1,2-dichloroethane, and if appropriate in the presence of an acceptor for hydrogen halide acids; an example of such an acceptor is a tertiary base such as pyridine.

According to a variant of the process, another functional derivative of the acid, for example an alkyl ester, can be reacted with the amine of formula $RNH_2$.

The following Examples illustrate the invention.

EXAMPLE 1

Desoxyvincaminamide

Code number: SL C 156

2.5 G (0.03 mol) of pyridine and 3.6 g. (2.5 ml; 0.03 mol) of thionyl chloride are added to a suspension of 9.7 g (0.03 mol) of desoxyvincaminic acid in 400 ml of dry benzene and this mixture is stirred for three hours an ambient temperature.

This mixture is then placed in an oilbath at 80° and whilst in the bath a stream of ammonia is passed through it for one hour. The mixture is cooled, the solvent is driven off in vacuo on a water-bath and the residue is rendered alkaline with 10% ammonia. The mixture is extracted with ethyl acetate, the organic layer is filtered over activated vegetable charcoal and the solvent is evaporated from the filtrate.

8.2 G (yield = 85%) of desoxyvincaminamide are thus obtained. This compound can be recrystallised from toluene or ethanol; melting point = 250°.

Analysis: $C_{20}H_{25}N_3O$ (mw. 323.4): Calculated: C, 74.26; H, 7.79; N, 12.99; O, 4.95%. Found: C, 74.09; H, 7.92; N, 13.17; O, 4.97%; C, 73.94; H, 7.93%.

The hydrochloride of desoxyvincaminamide is prepared by dissolving the base in alcohol and passing a stream of hydrogen chloride gas through this solution.

EXAMPLE 2

N-cyclopropyldesoxyvincaminamide

[($m$ = 1): Code No. S.L.D. 105]

2.5 Ml (0.03 mol) of pyridine followed by 2.5 ml (0.03 mol) of thionyl chloride are added to a suspension of 9.7 g (0.03 mol) of desoxyvinaminic acid in 100 ml of dry dichloroethane. The mixture is stirred for about 30 minutes and 2.3 g (0.04 mol) of cyclopropylamine are added to the solution so obtained, whilst cooling it with an icebath. The stirring is continued for three hours, the mixture is poured into 100 ml of 10% ammonia, the whole mixture is stirred vigorously and the organic layer is decanted, washed with water until neutral, dried over dry sodium sulphate and filtered through activated vegetable charcoal. The solvent is evaporated in vacuc on a water bath and the oily residue is chromatographed on a column of 100 g of Merck alumina of activity II–III, eluting with methylene chloride. The methylene chloride is driven off and the residue is triturated in 60 ml of cyclohexane whilst stirring vigorously for several hours to give 5.5 g (yield = 60%) of N-cyclopropyldesoxyvincaminamide: this is a water-insoluble compound which melts at 184°.

Analysis: $C_{23}H_{29}N_3O$ (mw 363.4): Calculated: C, 76.00; H, 8.04; N, 11.56; O, 4.41%; Found: C, 75.88; H, 7.99; N, 11.52; O, 4.59%; C, 76.01; H, 8.03; N, 11.60%.

EXAMPLE 3

N-cyclohexyldesoxyvincaminamide

[(m = 4): Code No. S.L.D. 135]

2.5 Ml (0.03 mol) of pyridine followed by 2.5 ml (0.03 mol) of thionyl chloride are added while stirring to a suspension of 9.7 g (0.03 mol) of desoxyvincaminic acid in 100 ml of dry 1,2-dichloroethane. This mixture is stirred for about 20 minutes until a solution is obtained and 4.1 g (0.04 mol) of freshly distilled cyclohexylamine are added whilst cooling with an icebath. Stirring is continued for 2 hours and 30 minutes, 100 ml of 10% ammonia are added, the mixture is stirred vigorously and the organic layer is decanted, washed with water until neutral and dried over sodium sulphate. It is filtered through activated vegetable charcoal, the solvent is evaporated in vacuo on a waterbath and the oily residue is chromatographed on a column of 150 g of Merck alumina of activity II–III, eluting with methylene chloride. The solvent is evaporated and the residue is triturated in 100 ml of cyclohexane. This mixture is stirred until precipitation is complete and the compound is filtered off and dried for three hours at 110°/10 mm to give 8.3 g (yield = 66.5%) of N-cyclohexyl-desoxyvincaminamide; this is a water-insoluble compound which melts at 208°.

Analysis: $C_{26}H_{35}N_3O$ (mw 405.6): Calculated: C, 76.99; H, 8.69; N, 10.36; O, 3.94%; Found: C, 77.02; H, 8.90; N, 10.36; O, 4.17%

EXAMPLE 4

N-cyclobutyldesoxyvincaminamide

[($m = 2$): Code No. S.L.D. 142]

2.5 Ml (0.03 mol) of pyridine followed by 2.5 ml (0.03 mol) of thionyl chloride are added while stirring to a suspension of 9.7 g (0.03 mol) of desoxyvincaminic acid in 100 ml of 1,2-dichloroethane. The solution rapidly turns rather brown. A solution of 5.5 g (0.05 mol) of cyclobutylamine hydrochloride in 15 ml of dry dimethylformamide is also prepared; 2.55 g (0.05 mol) of a 50% oily suspension of sodium hydride in mineral oil are added thereto and this mixture is stirred for 2 hours.

The solution of cyclobutylamine is added to the solution of desoxyvincaminic acid chloride, whilst cooling by means of a bath of ice water and whilst stirring.

The mixture is left for 3 hours at ambient temperature, then rendered alkaline with 100 ml of 10% ammonia and stirred vigorously for 15 minutes; the organic layer is decanted and washed with water until neutral, dried over sodium sulphate and filtered over activated vegetable charcoal, and the solvents are evaporated from the filtrate in vacuo on a water-bath. The residue is chromatographed on a column of 150 g of Merck alumina of activity II–III eluting with methylene chloride. The latter solvent is evaporated, the oily residue is dissolved in 250 ml of 0.5 N-hydrochloric acid and the base is reprecipitated by dropwise addition of 20% ammonia. The precipitate is filtered off, washed copiously with water and dried in a vacuum desiccator over phosphorus pentoxide to give 4.5 g (yield = 50%) of N-cyclobutyl-desoxyvincaminamide hemihydrate, melting at about 110° (pasty melting).

Analysis: $C_{24}H_{31}N_3O$. ½ $H_2O$ (mw 385.4): Calculated: C, 74.58; H, 8.34; N, 10.87%; Found: C, 74.54; H, 8.63; N, 10.90%.

EXAMPLE 5

N-cyclopentyldesoxyvincaminamide

[($m = 3$) Code No. S.L.D. 143]

2.5 Ml (0.03 mol) of pyridine following by 2.5 ml (0.03 mol) of thionyl chloride are added to a suspension of 9.7 g (0.03 mol) of desoxyvincaminic acid in 100 ml of 1,2-dichloroethane. 5.7 G (0.06 mol) of cyclopentylamine are added under a nitrogen atmosphere, whilst stirring and cooling by means of a bath of iced water; the nitrogen atmosphere, and the stirring are maintained for 3 hours. The mixture is rendered alkaline with 100 ml of 10% ammonia whilst stirring vigorously for 15 minutes. The organic layer is decanted, washed with water until neutral and dried over sodium sulphate. It is filtered through activated vegetable charcoal, the solvent is evaporated from the filtrate in vacuo on a waterbath and the oily residue is chromatographed on a column of 150 g of Merck alumina of activity II–III. Elution is carried out with methylene chloride, the latter is evaporated, the residue is dissolved in 250 ml of 0.5 N hydrochloric acid and the base is reprecipitated by slow addition of 20% ammonia. The precipitate is washed with water and dried in a vacuum desiccator over phosphorus pentoxide to give 5.3 g (yield = 60%) of N-cyclopentyldesoxyvincaminamide in the form of a monohydrate which melts at about 110° (pasty melting).

Analysis: $C_{25}H_{33}N_3O$. $H_2O$ (mw 407.4): Calculated: C, 73.50; H, 8.64; N, 10.28%; Found: C, 73.47; H, 8.67; N, 10.26%.

EXAMPLE 6

N-monocyclopropylapovincaminamide

[($m = 1$, $n = 0$), Code No. S.L.D. 121]

2.5 Ml of thionyl chloride and 2.5 ml of pyridine are added to 10 g (0.03 mol) of apovincaminic acid in 100 ml of 1,2-dichloroethane. This mixture is stirred for 15 minutes at ambient temperature and a solution of 2.3 g (0.04 mol) of cyclopropylamine in 25 ml of 1,2-dichloroethane is then added dropwise. This solution is stirred for four hours and the solvents are then evaporated in vacuo on a waterbath. The residue is dissolved in 300 ml of water, the solution is rendered alkaline with ammonia and the precipitate which formed is filtered off, washed with water and dried. It is recrystallised from the minimum amount of ethyl acetate to give 5.8 g (yield = 54%) of N-monocyclopropylapovincaminamide, melting at 210°.

EXAMPLE 7

N-monocyclohexylapovincaminamide

[($m = 4$, $n = 0$) Code No. S.L.D. 132]

2.5 Ml of thionyl chloride and 2.5 ml of pyridine are added to 10 g (0.03 mol) of apovincaminic acid in 100 ml of 1,2-dichloroethane. The mixture is stirred for 15 minutes at ambient temperature to give a limpid solution, and a solution of 4 g (0.04 mol) of cyclohexylamine in 40 ml of 1,2-dichloroethane is then added dropwise. This solution is stirred for four hours, the solvents are evaporated in vacuo on a waterbath, the residue is dissolved in 200 ml of water, the solution is rendered alkaline with ammonia, and the precipitate which formed is filtered off, washed with water and dried. It is recrystallised from the minimum amount of ethyl acetate to give 5.8 g (yield = 47.5%) of N-monocyclohexylapovincaminamide, melting at about 130°.

Analysis: $C_{26}H_{33}N_3O$ (mw 403.6): Calculated: C, 77.38; H, 8.24; N, 10.41%; Found: C, 76.81; H, 8.36; N, 10.30%.

EXAMPLE 8

N-cyclobutylapovincaminamide

[($m = 2, n = 0$), Code No. S.L.D.141]

11 G (0.1 mol) of cyclobutylamine hydrochloride are dissolved in 50 ml of anhydrous dimethylformamide and 5.1 g (0.1 mol) of a 50% oily suspension of sodium hydride are added to this solution. This mixture is stirred for twenty hours and a solution of apovincaminic acid chloride (previously prepared by mixing 20 g (0.062 mol) of apovincaminic acid, 5 ml of pyridine and 5 ml of thionyl chloride in 200 ml of 1,2-dichloroethane) is added slowly. The mixture is then left for 5 hours at ambient temperature whilst stirring vigorously. The sodium chloride is filtered off, the solvents are driven off from the filtrate, the residue is dissolved in water and the aqueous solution is rendered alkaline with ammonia. The precipitate which has separated out is filtered off, washed with water, dried and recrystallised from the minimum amount of ethyl acetate to give 7.5 g (yield = 32%) of N-cyclobutylapovincaminamide, melting at 208°

Analysis: $C_{24}H_{29}N_3O$ (m.w. 375.52): Calculated: C, 76.77; H, 7.78; N, 11.19; O, 4.26%; Found: C, 76.76; H, 7.75; N, 11.05; O, 4.52%.

EXAMPLE 9

N-cyclopentylapovincaminamide

[($m = 3, n = 0$), Code No. S.L.D.149]

5 Ml of thionyl chloride and 5 ml of pyridine are added successively to a suspension of 20 g (0.062 mol) of apovincaminic acid in 200 ml of dry 1,2-dichloroethane to give a solution, which is stirred for 15 minutes and to which 6.8 g (0.08 mol) of cyclopentylamine dissolved in 70 ml of dry 1,2-dichloroethane are added dropwise. This mixture is stirred for 4 hours at ambient temperature, the solvents are evaporated in vacuo on a waterbath, the oily residue is dissolved in 1.5 liter of water and the aqueous solution is rendered alkaline with concentrated ammonia. The precipitate which formed is filtered off, washed with water and dried over phosphorus pentoxide. It is recrystallised from the minimum amount of ethyl acetate to give 11.2 g (yield = 46%) of N-cyclopentyl-apovincaminamide, melting at 175°.

Analysis: $C_{25}H_{31}N_3O$ (m.w. 389.5); Calculated: C, 77.08; H, 8.02; N, 10.79%; Found: C, 77.11; H, 8.28; N, 10.70%.

EXAMPLE 10

N-cyclopropylmethylapovincaminamide

[$m = 1, n = 1$, Code No. S.L.D.158]

5 Ml of thionyl chloride and 5 ml of pyridine are added successively to a suspension of 20 g (0.062 mol) of apovincaminic acid in 200 ml of dry 1,2-dichloroethane. 6.3 G (0.08 mol) of cyclopropylmethylamine dissolved in 65 ml of 1,2-dichloroethane are added dropwise to the limpid solution, which is stirred for 15 minutes. The mixture obtained is stirred for four hours at ambient temperature, the solvents are evaporated and the oily residue is dissolved in one liter of water. The aqueous solution is rendered alkaline with ammonia and decanted from a gum which deposited at the bottom of the flask. This gum is re-triturated in one liter of water, the mixture is reacidified until the gum has dissolved and the product is again precipitated by adding ammonia whilst stirring vigorously. The crystals which formed are filtered off, washed with water until the washings are neutral and dried in a desiccator over phosphorus pentoxide to give 12 g (yield = 52%) of N-cyclopropylmethyl-apovincaminamide, which are recrystallised from the minimum amount of ethyl acetate.

The compounds of the invention were subjected to various pharmacological tests.

Acute toxicity

The compounds were administered orally to mice of the CD1 strain. The mortality was recorded over 7 days and the 50% lethal doses ($LD_{50}$) were determined graphically.

The toxicities on intraperitoneal and intravenous administration were determined in accordance with the method of Miller and Tariter (Proc. Soc. Exp. Biol. Med. 1944- vol 57, page 261).

TABLE

| Compounds | $LD_{50}$ (mg/kg) in mice (compounds tested in a solution containing ascorbic acid) | | |
|---|---|---|---|
| | intravenous | intraperitoneal | oral |
| SLC 156 | 109 | 210 | 607 |
| SLD 105 | 76 | 165 | 290 |
| Vincamine | 75 | 215 | 460 |

Anoxia test on mice under low (oxygen) pressure conditions

Mice of strain CD1 are kept in an atmosphere depleted in oxygen, by producing a partial vacuum (190 mm of mercury, corresponding to 5.25% of oxygen).

The survival time of the animals is noted. This time is increased by agents capable of assisting tissue oxygenation and in particular cerebral oxygenation. The compounds studied are administered in several doses intraperitoneally 10 minutes before the test. The percentage increases in the survival time relative to the values obtained with control animals are calculated. The mean active dose (MAD), the dose which increases the survival time by 100%, is determined graphically.

The results obtained are summarised in the Table

TABLE

| Compound | Protective activity in the test of anoxia under reduced pressure conditions (in mice) MAD (mg/kg) |
|---|---|
| SLC 156 | 1.8 |
| SLD 105 | 1 |
| SLD 121 | 2.5 |
| SLD 142 | 0.5 |
| Vincamine | 8 |

The above results show that the therapeutic indices of the compounds are good.

Furthermore, according to the toxicity Table, the ratio of the $LD_{50}$ for oral administration to the $LD_{50}$ for intravenous administration is low in the case of compound SLD 105; accordingly, the resorption of this compound by the digestive tract is good.

The compounds of the invention are useful in human and veterinary medicines, especially in the field of circulatory insufficiencies and in the cerebral vascular field.

The invention provides a pharmaceutical composition comprising a compound of the invention or a salt thereof as the active principle and a pharmaceutically acceptable carrier or diluent, particularly those suitable for oral or parenteral administration. These pharmaceutical compositions can also contain other medicinal substances with which the compound is pharmacologically and therapeutically compatible.

The pharmaceutical compositions can contain also ascorbic acid, either in the form of the free acid or in the form of one of its known salts or in the form of a complex such as an equimolecular complex of ascorbic acid with nicotinamide or an equimolecular complex of ascorbic acid with pyridoxine, these combinations having the advantage of permitting better resorption of the compound of the invention by the digestive tract.

For oral administration, all the usual forms can be used; examples are tablets, dragees, pills, capsules, cachets and potable solutions or suspensions, in which the unit weight of active principle is suitably 0.5 to 25 mg and the daily dose is suitably 0.5 to 100 mg.

For parenteral administration, solutions prepared beforehand or immediately prior to use and buffered to a physiological pH can be employed. These solutions suitably contain 0.5 to 20 mg of active principle in a volume of 1 to 5 ml. In practice, the solutions are divided into ampoules of 1 to 5 ml capacity for intramuscular or intravenous injection, or for administration by slow intravenous infusion. The daily dose for parenteral administration can be 0.5 to 100 mg.

We claim:

1. A compound of general formula

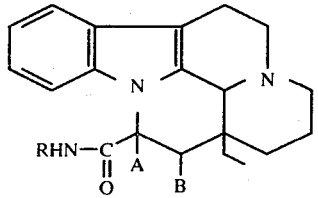

wherein A and B are both hydrogen atoms and R is a hydrogen atom or a

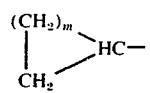

group, or A and B together represent an additional bond and R is a

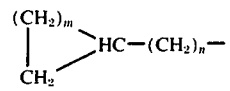

radical, m being 1, 2, 3 or 4 and n being 0, 1, 2 or 3, or a pharmaceutically acceptable acid addition salt thereof.

2. A compound as claimed in claim 1 which is desoxyvincaminamide or a pharmaceutically acceptable acid addition salt thereof.

3. A compound as claimed in claim 1 which is desoxyvincaminic acid N-monocyclopropylamide or a pharmaceutically acceptable acid addition salt thereof.

4. A compound as claimed in claim 1 which is desoxyvincaminic acid N-monocyclobutylamide or a pharmaceutically acceptable acid addition salt thereof.

5. A compound as claimed in claim 1 which is desoxyvincaminic acid N-monocyclopentylamide or a pharmaceutically acceptable acid addition salt thereof.

6. A compound as claimed in claim 1 which is desoxyvincaminic acid N-monocyclohexylamide or a pharmaceutically acceptable acid addition salt thereof.

7. A compound as claimed in claim 1 which is N-monocyclopropylapovincaminamide or a pharmaceutically acceptable acid addition salt thereof.

8. A compound as claimed in claim 1 which is N-monocyclobutylapovincaminamide or a pharmaceutically acceptable acid addition salt thereof.

9. A compound as claimed in claim 1 which is N-monocyclopentylapovincaminamide or a pharmaceutically acceptable acid addition salt thereof.

10. A compound as claimed in claim 1 which is N-monocyclohexylapovincaminamide or a pharmaceutically acceptable acid addition salt thereof.

11. A compound as claimed in claim 1 which is N-cyclopropylmethylapovincaminamide or a pharmaceutically acceptable acid addition salt thereof.

12. A pharmaceutical composition suitable for treating pathological disturbances in mammals and involving an anoxia factor, consisting essentially of an effective amount of a compound or salt of claim 1, and a pharmaceutically acceptable carrier or diluent.

13. A composition as claimed in claim 12 containing also ascorbic acid, either in the form of the free acid or a salt, or in the form of a complex.

14. A composition as claimed in claim 13 wherein the complex is an equimolecular complex of ascorbic acid with nicotinamide or an equimolecular complex of ascorbic acid with pyridoxine.

15. A method of treating pathological disturbances in mammals and involving an anoxia factor, the method consisting essentially of the step of administering to the mammal an effective amount of a compound or salt as claimed in claim 1.

* * * * *

UNITED STATES PATENT AND TRADEMARK OFFICE
CERTIFICATE OF CORRECTION

PATENT NO. : 4,011,330
DATED : March 8, 1977
INVENTOR(S) : Don Pierre René Lucien GIDUICELLI et al.

It is certified that error appears in the above-identified patent and that said Letters Patent are hereby corrected as shown below:

On the first page of the patent under "[30] Foreign Application Priority Data", add the following:

June 6, 1975.......75.17670

Signed and Sealed this

Fourteenth Day of June 1977

[SEAL]

Attest:

RUTH C. MASON
*Attesting Officer*

C. MARSHALL DANN
*Commissioner of Patents and Trademarks*